US005836933A

United States Patent [19]

Buttitta et al.

[11] Patent Number: 5,836,933

[45] Date of Patent: Nov. 17, 1998

[54] PARENTERAL FLUID DELIVERY BAG WITH INTEGRAL LINE SET

[75] Inventors: Anthony D. Buttitta; John M. Munsch, both of Libertyville; Ying-Cheng Lo, Green Oaks; Marc Bellotti, Libertyville, all of Ill.

[73] Assignee: Baxter International, Inc., Deerfield, Ill.

[21] Appl. No.: 666,190

[22] Filed: Jun. 19, 1996

(Under 37 CFR 1.47)

[51] Int. Cl.[6] .......... A61B 19/00

[52] U.S. Cl. .......... 604/403; 604/408; 604/411; 604/414

[58] Field of Search .......... 383/41, 66, 904, 383/906; 206/436, 438, 570; 604/403, 404, 408–410, 411, 414–416

[56] References Cited

U.S. PATENT DOCUMENTS

| | | | |
|---|---|---|---|
| 1,546,016 | 7/1925 | Eisele | 604/410 |
| 2,789,728 | 4/1957 | Britton | 383/906 |
| 2,955,595 | 10/1960 | Semple | 604/409 |
| 3,306,327 | 2/1967 | Ilg | 383/66 |
| 3,307,549 | 3/1967 | Zackheim . | |
| 3,383,017 | 5/1968 | Krings | 383/66 |
| 3,473,703 | 10/1969 | Lippincott | 383/906 |
| 4,818,122 | 4/1989 | Arbuthnot | 383/41 |
| 4,976,707 | 12/1990 | Bodicky et al. | 604/410 |
| 5,163,554 | 11/1992 | Lampropoulos et al. | 206/438 |
| 5,289,858 | 3/1994 | Grbenkort | 604/403 |
| 5,314,421 | 5/1994 | Leuenberger | 604/403 |
| 5,423,793 | 6/1995 | Isono et al. | 604/403 |
| 5,445,629 | 8/1995 | Debrauwere et al. | 604/408 |

FOREIGN PATENT DOCUMENTS

| | | |
|---|---|---|
| 0616064 | 1/1961 | Italy . |

*Primary Examiner*—Robert A. Clarke
*Assistant Examiner*—David J. Cho
*Attorney, Agent, or Firm*—Francis C. Kowalik

[57] ABSTRACT

A parenteral fluid delivery bag having a line set formed integral with the bag, the line set being peelably releasable from the remainder of the bag so as to assume a deployed position adapted to enter into fluid communication with a patient. In an alternate embodiment, a plurality of bags connected by an integrally formed wye-junction are adapted for delivery to a patient and retrieval of fluid from a patient.

17 Claims, 3 Drawing Sheets

PARENTERAL FLUID DELIVERY BAG WITH INTEGRAL LINE SET

FIELD OF THE INVENTION

The instant invention relates to drug delivery bags and, more specifically, to I.V. bags.

BACKGROUND OF THE INVENTION

The general I.V. bag is well known in the art Such a bag has an envelope which contains a fluid. This fluid either contains a medicament or the bag is arranged to allow a medicament to be added to the fluid contained within the bag. These bags come equipped either with septa or some other docking means so as to allow a line set to be attached. To prevent air infiltration of the patient, the line set must then be purged or primed. Furthermore, after the medicament has been delivered to the patient, the line set must be flushed or purged before an additional or different medicament can be added. This is a time consuming procedure and, in this time of rising costs, any gain in efficiency of the staff is welcome.

U.S. Pat. No. 3,307,549 to Zackheim discloses an enema bag which has an extended fluid chamber serving as an enema tube. This device does not contemplate either a fluid reservoir and extensible line set formed from two webs or a peelably releasable set as disclosed in the instant invention.

U.S. Pat. No. 5,466,322 to Munsch describes an elongate plastic member, or tube, which is fused to an adjacent member and is subsequently peelable from an adjoining member. The invention does not, however, disclose a bag and line set formed integral as in the instant invention.

SUMMARY OF THE INVENTION

The instant invention contemplates a fluid delivery bag having a prefilled line set formed integral with the bag in use, in the first embodiment thereof, the invention would be arranged for delivery of the fluid contained therein and the integral line set would be peelably released from the associated web. A suitable fluid communication device would be attached to the fitment resident at the distal end thereof so as to place the bag in fluid communication with the patient In the second embodiment of the instant invention a plurality of co-formed bags are used wherein a first bag contains a fluid and a second bag is initially empty. The bags are connected by an integrally formed y-shaped line set thereby placing both bags in alternate fluid communication with a single delivery tube wherein the delivery tube has associated therewith a fitment. The most common use of a dual bag or multi-bag arrangement being continuous ambulatory peritoneal dialysis wherein the first bag would contain a dialyzing fluid and the second bag would be used to hold used dialyzing fluid.

Therefore, it is a primary object of the invention to provide for a fluid delivery bag with an integral line set.

It is a further object of the invention to provide for a fluid delivery bag and line set combination which is pre-filled with fluid.

It is another object of the invention to provide for a bag and line set which is co-disposable.

It is a further object of the invention to provide for the elimination of the necessity of purging the line set of medicament.

It is a further object of the instant invention to allow for a bag and line set to be co-formed in a single operation.

In an embodiment, it is a further object of the invention to provide a mixing chamber for adding a medicament to a diluent fluid wherein the mixing chamber is integral with the delivery line.

In an embodiment it is a primary object of the instant invention to provide for a co-formed bag set operative to alternately deliver and receive fluid from a patient.

These, and other objects of the instant invention, will become obvious in the detailed description of the preferred embodiments and claims appended hereto.

BRIEF DESCRIPTION OF THE DRAWINGS

is

DETAILED DESCRIPTION OF THE PREFERRED EMBODIMENTS

Figure 1:
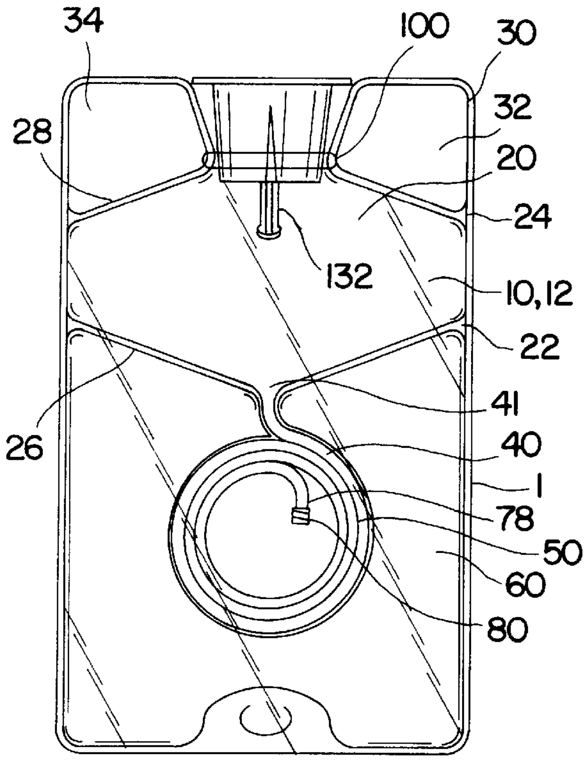
FIG. 1 is a plan view of the novel bag.

As shown in FIG. 1, an assembly 1 is disclosed which is formed of a plurality of polymeric sheets or sheet webs 10 and 12 wherein the sheets can be of a polyvinylchloride, polyolefin or other flexible, liquid-tight, and biocompatible material.

The sheets are formed into a reservoir 20 capable of containing a medicament or a suitable diluent or other fluid. Reservoir 20 is defined by a plurality of welded seals 22, 24, 26, and 28 wherein the seals are operative to separate the reservoir 20 from the rest of the bag assembly 1.

Seals 22, 24, 26, and 28 are preferentially made by radio-frequency welding, but may be made by any other suitable process for making parenteral fluid delivery bags. The reservoir is further defined by a peripheral seal 30 which is formed about the outer edge of the bag assembly 1 and is operative to enclose the outer edges of reservoir 20 in cooperation with seals 22, 24, 26 and 28.

Figure 2:
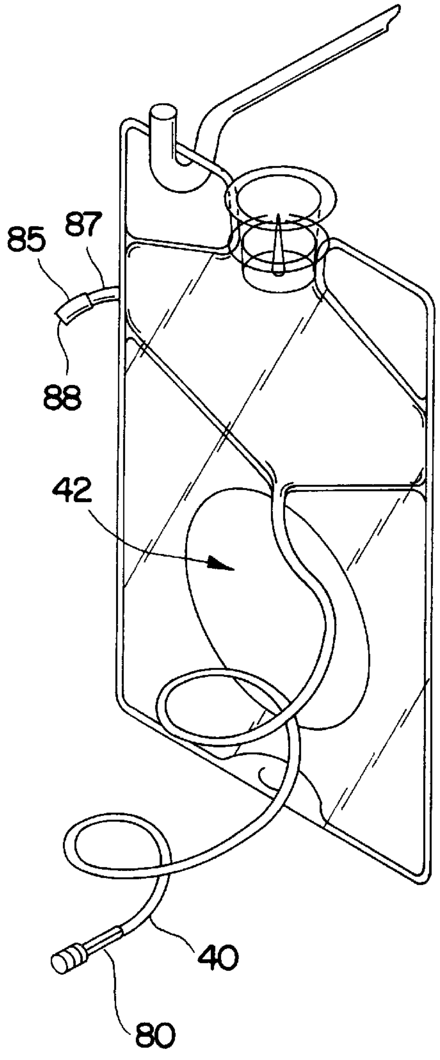
FIG. 2 is a perspective view of the novel bag with the integral inset deployed and the bag hanging in the preferred orientation for delivery of a fluid.
Figure 3:
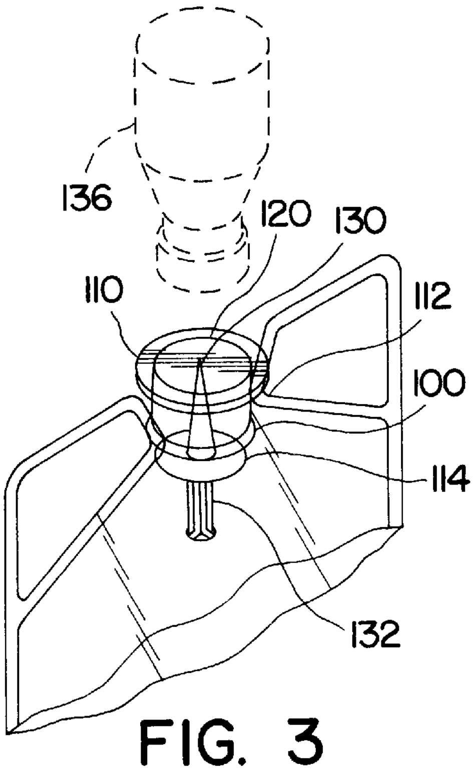
FIG. 3 is a perspective view of the drug introducer.
Figure 4:
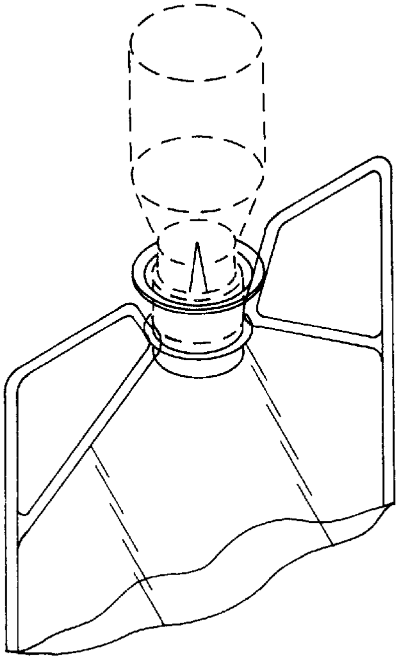
FIG. 4 is a perspective view of the introducer with a medicament bottle affixed.
Figure 5:
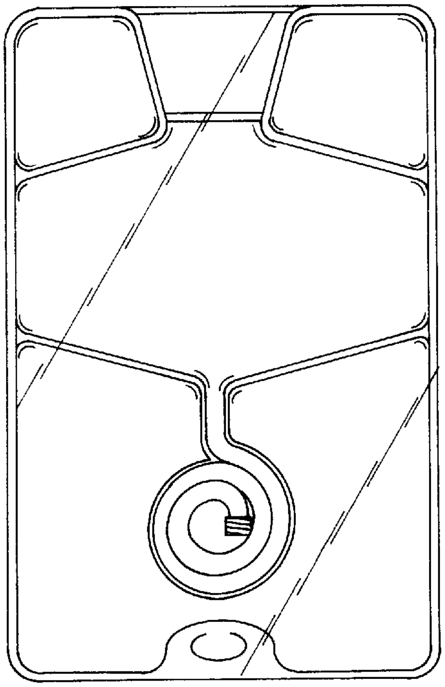
FIG. 5 is a plan view of the novel bag in the pre-filled embodiment thereof.
Figure 6:
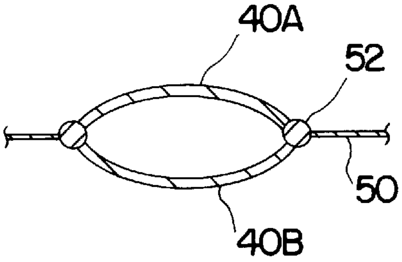
FIG. 6 is a cross-sectional view of the line set
Figure 7:
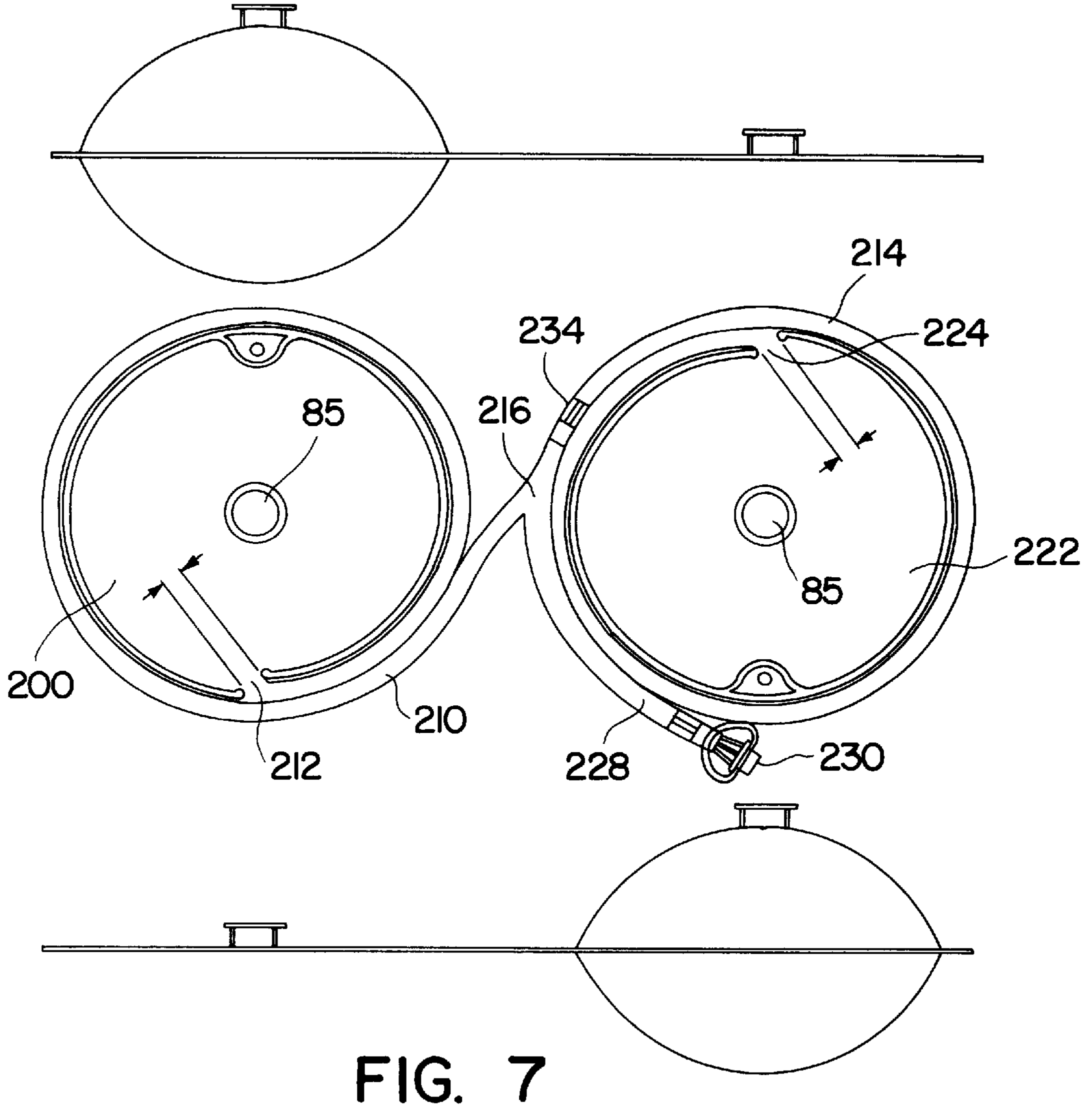
FIG. 7 is a plan view of the dual bag embodiment of the invention.

The perimeter seal 30 also defines, in cooperation with the first upper reservoir seal 24 and the second upper reservoir seal 28, a first hanging aperture 32 and a second hanging aperture 34 which are operative to engage a bag hanger 200, as shown in FIG. 2, thereby orienting the bag assembly 1 correctly for administration of the fluid or medicament contained in, or introduced to, reservoir 20.

Line set 40 is formed integral or unitary with reservoir 20 and bag assembly 1, and is in fluid communication with reservoir 20 via port 41. The integral line set 40 is co-formed with bag 1 and is releasably attached thereto by a tearable seal 50. To deploy the line set 40, an operator, such as a nurse, would grasp the distal end 78 of the line set 40 and draw the distal end 78 away from the bag assembly 1, thereby releasing the tear seal 50 of the line set 40 and drawing the line set 40 out of the line set aperture 42 defined by the bag web 60 to which the line set 40 is attached via tear seal 50.

In the pictured embodiment, line set 40 is spiral wound within web 60, and displays a continuous spiral tear seal 50.

The instant invention contemplates a variety of line set layouts within web 60, including, but not limited to, sinusoidal or folded s-shaped arrangements when the line set 40 is undeployed.

Line set 40 is composed of a first envelope section 40A and a second envelope section 40B. In this embodiment the envelope sections are formed from sheets 10 and 12, out of which the rest of the bag assembly 1 is also formed.

In an embodiment, line set 40, consisting of envelopes 40A and 40B, is formed by sealing the first envelope 40A to the second envelope 40B forming fluid seal 52. Exterior to the fluid seal 52 is tear seal 50 as aforedescribed, thereby allowing deployment of line set 40 whilst maintaining integrity of the line set 40.

The distal end or terminus 79 of the line set 40 is fused or otherwise connected to an appropriate connector or fitment 80 which may be a septum, or luer fitting, or frangible connector, or some other connector or combination thereof suitable for intravenous delivery of fluids. Additionally, line set 40 is filled with fluid also resident in chamber 20, thereby eliminating the necessity of purging the line set of air as aforementioned.

Associated with the chamber 20, and in fluid communication therewith, is a fill port 85 through which fluid is introduced into the chamber 20. Fill port 85 is subsequently sealed by plug 88, thereby closing off port 85 and fill tube 87. Alternatively, and preferred, the line set 40 may be used as a fill port prior to connecting the appropriate connector 80 to the line set 40. In an embodiment herein preferred, also associated with chamber 10, is a medicament introduction port 110 which is attached to bag 1 at support ring 100. Support ring 100 is formed with the rest of bag 1 and is operative to support introduction port 110 in a suitable position for administering a medicament from another container into chamber 20. In the preferred embodiment, introduction port 110 is a spike connector, wherein the spike connector 110 has a connector cup 112 in contact with support ring 100 and a cup bottom 114, the exterior side of which is in contact with the interior of chamber 20. Also associated with connector 110 is an interior spike 130, said spike 130 being in fluid communication with chamber 20 subsequent to opening frangible plug 132.

In operation, protective film 120 is removed exposing spike connector 130. A suitable medicament containing vial 136 is impaled on spike connector 130. Then frangible 132 is broken, allowing fluid communication between chamber 10 and the medicament containing vial 136, allowing the medicament in vial 136 to be introduced to a patient via line set 40.

In the alternate embodiment of the invention a first fluid containing bag 200 has wrapped therearound a substantially helically wound line set 210 which is in fluid communication with the bag 200 by means of a fluid orifice 212. The line set 210 joins a second drainage line set 214 at a wye-junction 216 wherein the second leg of the wye 218 is integral with a drainage line 220 which is helically wound about drainage bag 222 and is formed integral therewith. Drainage line 220 is in fluid communication with drainage bag 222 by means of a drain orifice 224 at the proximal end 226 of the drain line 220.

The base of wye-junction 216 defines a common delivery and drain line 228, the distal end of which comprises an appropriate fitment 230. Inserted within the delivery line 220 and the drain line 228 are frangible plugs 232, 234 which are operative to provide a uni-directional flow of fluid from the delivery bag 200 to the patient and subsequently from the patient into drain bag 222.

In operation in this embodiment of the invention an operator would deploy both the delivery line 220 and the drain line 228. The operator would then break the delivery line frangible plug after connecting the fitment to the patient thereby allowing fluid to flow from the delivery bag 200 to the patient. When the delivery therapy is complete, the operator would then break frangible plug 234 which is associated with drain line 228 thereby allowing fluid to drain from the patient into the receiving or drain bag 222.

The aforewritten detailed description is illustrative of the preferred embodiment of the instant invention and is not meant to present limitations on the instant invention aside from those in the claims appended hereto.

In accordance with our invention, we claim:

1. A bag for communicating fluids with a patient comprising a fluid chamber, a line set formed unitary with said fluid chamber and a bag web having a peelably releasable line set co-formed with said web and a line set aperture defined by said web and a tear seal between said web and said line set, wherein said aperture is opened by said line set being extended from said web by parting said tear seal from said web.

2. The bag according to claim 1 and said line set having an initial compactly coiled aspect.

3. The bag according to claim 2 and said line set further being deployable into an elongate position.

4. The bag according to claim 2 and said bag further comprising, said tear seal operative to maintain said line set in said compact aspect.

5. The bag according to claim 3 and said tear seal further being releasable so as to effect said deployment of said line set.

6. The invention according to claim 5 and said line set further comprising a plurality of sheet webs wherein said bag, reservoir and line set are comprised of said webs.

7. The bag according to claim 4 and said line set further comprising a fluid seal, said fluid seal being substantially co-extensive with said tear seal.

8. The bag according to claim 6 and a fluid seal wherein said webs and said fluid seal define a lumen, interior to said line set.

9. A bag for parenteral administration of fluids, said bag comprising means for retaining a fluid within said bag and, unitary with said fluid retaining means, means for administering said fluid parenterally wherein said means for administering said fluid is releasably retained to said fluid retaining means by a web unitarily co-formed with said fluid retaining means and said means for administering said fluid.

10. The bag according to claim 9 and means for introducing a medicament into said means for retaining a fluid.

11. The bag according to claim 9 and said means for administering a fluid parenterally, further comprising extensible means for delivering said fluid from said means for retaining said fluid and, wherein said extensible means has a terminus remote from said means for retaining a fluid and there is a fitment adapted to be in parenteral fluid communication with a patient, said terminus being adapted to enter into fluid communication with said fitment.

12. The bag according to claim 11 and said terminus including a frangible plug therewithin.

13. The bag according to claim 12 and said extensible means providing fluid communication between a plurality of said fluid retaining means to a single terminus.

14. The bag according to claim 10 and said means for introducing a medicament further comprising a spike connector and a frangible plug associated with said spike connector.

15. A method for delivering a fluid to a patient comprising the following steps:

(a) wherein there is a bag having a web associated therewith said bag containing the fluid to be administered and said bag has a preferred orientation for delivery of said fluid, orienting said bag into said preferred position;

(b) wherein said bag has a line set formed unitary with said bag and said line set is deployable, deploying said line set by releasing said line set from said bag web;

(c) wherein said line set has a distal end and said distal end is adaptable to be put into fluid communication with said patient, establishing said communication; and (d) delivering said fluid to said patient.

16. The method of claim 15 and wherein there is a second bag in alternate fluid communication with said patient, placing said second bag in fluid communication with said patient.

17. The method according to claim 16 and wherein said second bag is adapted to receive fluid from said patient, receiving said fluid in said second bag.

* * * * *